United States Patent
Dowlatshahi et al.

[11] Patent Number: 5,569,240
[45] Date of Patent: Oct. 29, 1996

[54] APPARATUS FOR INTERSTITIAL LASER THERAPY

[75] Inventors: Kambiz Dowlatshahi; Charles K. Rhodes, both of Chicago, Ill.

[73] Assignee: Kelsey, Inc., Chicago, Ill.

[21] Appl. No.: 479,241

[22] Filed: Jun. 7, 1995

Related U.S. Application Data

[63] Continuation of Ser. No. 182,452, Jan. 13, 1994, abandoned, which is a continuation of Ser. No. 988,219, Dec. 8, 1992, abandoned, which is a division of Ser. No. 534,931, Jun. 8, 1990, Pat. No. 5,169,396.

[51] Int. Cl.$^6$ .................................................. A61B 17/32
[52] U.S. Cl. ................................................................ 606/15
[58] Field of Search ................................ 606/14, 15, 16, 606/17, 1, 4, 5, 6, 31; 128/736

[56] References Cited

U.S. PATENT DOCUMENTS

| | | | |
|---|---|---|---|
| 1,968,997 | 5/1932 | Drucker | 604/21 |
| 4,222,375 | 9/1980 | Martinez | 604/20 |
| 4,402,311 | 9/1983 | Hattori | 128/736 |
| 4,559,942 | 12/1985 | Eisenberg | 606/16 |
| 4,662,368 | 5/1987 | Hussein et al. | 606/15 |
| 4,665,927 | 5/1987 | Daily | 128/736 |
| 4,773,413 | 9/1988 | Hussein et al. | 606/15 |
| 4,819,630 | 4/1989 | De Hart | 606/15 |
| 4,950,267 | 8/1990 | Ishihara et al. | 606/12 |
| 4,957,481 | 9/1990 | Gatenby | 606/10 |
| 4,959,063 | 9/1990 | Kojima | 606/15 |
| 5,019,075 | 5/1991 | Spears et al. | 606/7 |
| 5,125,925 | 6/1992 | Lundahl | 606/15 |
| 5,129,896 | 7/1992 | Hasson | 606/15 |
| 5,242,437 | 9/1993 | Everett et al. | 606/15 |
| 5,312,392 | 5/1994 | Hofstetter et al. | 606/2 |
| 5,330,517 | 7/1994 | Mordon et al. | 607/89 |

FOREIGN PATENT DOCUMENTS

| | | | |
|---|---|---|---|
| 2826383 | 12/1979 | Germany | 606/16 |
| 8704611 | 8/1987 | WIPO | 606/15 |

*Primary Examiner*—Gary Jackson
*Assistant Examiner*—Sonya Harris-Ogugua
*Attorney, Agent, or Firm*—Robert J. Schneider; Keck, Mahin & Cate

[57] ABSTRACT

Apparatus and method for locally generating hyperthermia-induced coagulation necrosis in tissue masses located deeply within the body of a subject. High energy laser radiation is introduced into the target tissue mass using an optical fiber inserted into a metallic cannula through which a suitable fluid is coaxially flowed. A combination of the fluid flow and the slow withdrawal of the cannula/fiber combination during therapy protects the optical fiber tip, thereby preserving its energy transmission characteristics. After establishment of a small fluid bolus in front of the fiber tip, fluid flow which is approximately proportionate to the laser energy employed has been found to be most effective in this regard.

4 Claims, 1 Drawing Sheet

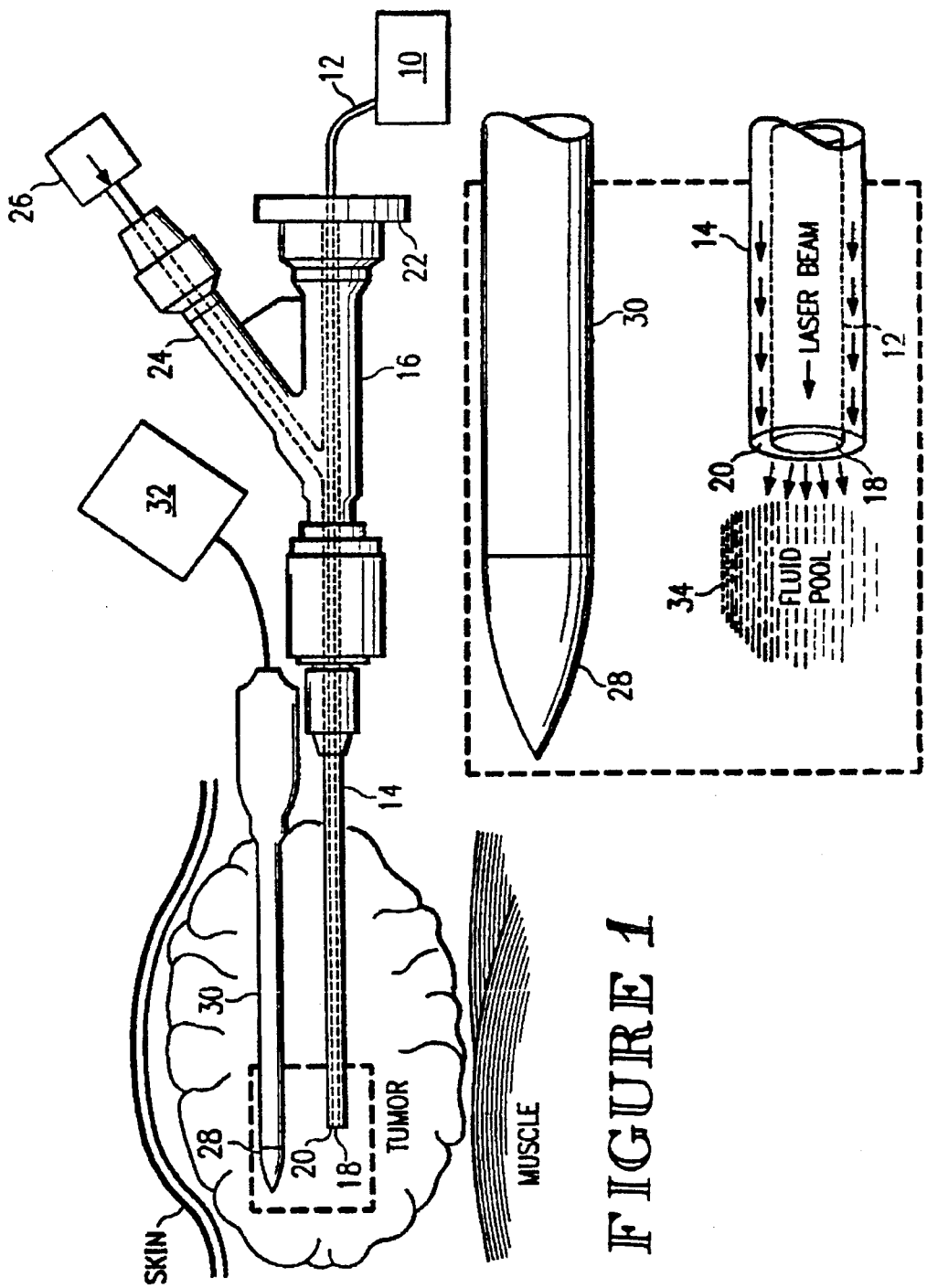

APPARATUS FOR INTERSTITIAL LASER THERAPY

This is a file wrapper continuation of application Ser. No. 08/182,452 filed on Jan. 13, 1994, now abandoned, which is a file wrapper continuation of application Ser. No. 07/988,219 filed on Dec. 8, 1992, now abandoned, which is a divisional of parent application Ser. No. 07/534,931 filed on Jun. 8, 1990, now U.S. Pat. No. 5,169,396.

BACKGROUND OF THE INVENTION

The present invention relates generally to the therapeutic use of laser radiation, and more particularly to the interstitial application of laser radiation therapy to tissue masses.

Non-contact treatment of malignant tumors by laser irradiation, predominantly using Nd:YAG lasers, has been practiced for more than a decade, and significant numbers of reports concerning its effectiveness as a procedure exist. Patients having advanced esophageal, bronchial, colorectal and bladder tumors, have been successfully palliated using this technique. Researchers have also tested the possibility of treating more deeply located tumors by inserting the laser probe, either alone or through a needle, into the lesion. This interstitial method of coagulation by hyperthermia with subsequent coagulative necrosis, however, has been hampered by damage to the tip of the fiberoptic probe with consequent loss of laser energy transmission. The damage has been found to be the consequence of adhesion of the heated tissue to the quartz fiber with resulting charring thereof, and the subsequent absorption of intense laser energy at the interface. Defacing of the fiber tip has been observed. This problem has been partially overcome by: a. reducing the laser output power from the 20–40 Watt range to 0.5–2.0 Watts while simultaneously increasing the irradiation exposure time; b. coating the probe tip with sapphire which has a higher melting point than quartz and also diffuses the light; or c. inserting the fiber into a plastic sheath with circulating coolant fluid within the sheath around the fiber tip.

The article entitled "Nd:YAG Laser-Induced Interstitial Hyperthermia Using A Long Frosted Contact Probe," by Masoud Panjehpour et al., published in Lasers In Surgery And Medicine 10, 16 (1990), identifies the need to apply laser radiation interstitially rather than to the surface of a tumor in hyperthermic treatment of any sizable tissue masses. The authors describe a frosted contact probe utilized to diffuse the laser light over the entire area of the frosted length, thereby reducing the power density at the tip while providing sufficient heating. Insignificant histological changes are reported from treatments at power levels as high as 4 Watts. However, at a 5 Watt power level, after 30 min. of irradiation, some level of necrosis occurred.

In U.S. Pat. No. 4,669,465, for "Laser Catheter Control And Connecting Apparatus" issued to Gary L. Moore et al. on Jun. 2, 1987, the inventors teach an angioplasty catheter apparatus for delivering laser light to obstructions in blood vessels. A light transmitting optical fiber is inserted into an elastic tube through which saline solution is passed coaxially with the fiber and out the end thereof from which the laser light is emitted. The saline solution is infused continuously during the laser operation with the initiation of the infusion being shortly prior to the irradiation process in order to provide greater fluid clarity during the irradiation, to provide a better medium for the laser energy at the site, and to carry away debris formed as a result of the procedure, thereby keeping the laser fiber tip and the zone immediately adjacent thereto substantially free of such debris. Moreover, the inventors teach that during the laser operation, the fiber tip is advanced through the substance to be removed, and that irradiation must not occur while the tip of the lasing fiber is retracted within the catheter. The elastic catheter is tipped with an inflatable balloon, rendering the entire apparatus suitable only for insertion into orifices and vessels.

In the articles entitled "Tumor Therapy With Hematoporphyrin Derivative And Lasers Via A Percutaneous Fiberoptic Technique: Preclinical Experiments," by R. A. Gatenby, N. D. Hammond, and D. Q. Brown, Radiology 163, 163 (1987), and "CT Guided Laser Therapy In Resistant Human Tumors: Phase I Clinical Trial," by R. A. Gatenby et al., Radiology 163, 172 (1987), the authors teach the insertion of a 400 micron diameter optic al fiber having a terminal cylindrical diffuser into a flexible teflon sheath catheter which is then inserted in to tumors. The tissue to be treated is first sensitized using a hematoporphyrin derivative, and a maximum power of 1.2 Watts from an argon ion laser-pumped dye laser emitting wavelengths greater than 600 nm is employed to photolyze the hematoporphyrin thereby producing chemically active species which interact with the tissue mass. An average of 900 Joules of energy were applied resulting in a mean temperature rise in the tumor of 9° C. Therefore, there was some response of the tumor to hyperthermia, although the authors report that the principal effect was chemical. No blood clot adherence to the optical fiber with consequential charring was observed, presumably as a result of the low output power and the diffuse nature of the laser light.

In "In Depth Radiation Therapy by YAG Laser For Malignant Tumors In The Liver Under Ultrasonic Imaging," by D. Hashimoto, M. Takami, and Y. Idezuki, Gastroenterology 88, 1663 (1985), the authors describe precise localization and needle diagnosis of lesions deeply located in various organs using radiographic, sonographic and computerized tomographic techniques. However, there is no teaching of the use of such needles as part of the laser therapy procedure.

Accordingly, it is an object of the present invention to provide an apparatus and met hod for treatment of solid tumors located in various organs by laser-induced hyperthermia with subsequent coagulative necrosis without the usual concern that laser energy transmission to the target tissue mass would degrade as the procedure is continued.

Another object of our invent ion is to provide an apparatus and method for efficient and rapid treatment of sol id tumors located in various organs by laser-induced hyperthermia with subsequent coagulative necrosis.

Yet another object of the present invention is to provide an apparatus and method for treatment of solid tumors located in various organs by laser-induced hyperthermia with subsequent coagulative necrosis while inducing a minimum of damage to surrounding, healthy tissue.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

To achieve the foregoing and other objects and in accordance with the purpose of the present invention, as embodied and broadly described herein, the apparatus of this invention includes a thin metallic cannula for insertion into a tissue mass, a laser for generating light having a chosen wavelength and intensity, an optical fiber for receiving and transmitting the laser light to the tissue mass, whereby the optical fiber is inserted into the cannula such that a chosen physiologically acceptable fluid may be flowed coaxially between the cannula and the optical fiber. Preferably, heat sensing means located in the vicinity of the end of the cannula a reprovided for determining the effects of the laser light on the tis sue mass. It also preferred that the physiologically acceptable fluid includes a dye which absorbs the laser radiation.

In a further aspect of the present invention, accordance with its objects and purposes, the method here of includes insertion of a thin metallic cannula within which an optical fiber for guiding laser light having a chosen wavelength and intensity may be longitudinally adjusted, and through which cannula a chosen physiologically acceptable fluid may be flowed, into a tissue mass to be treated, flowing fluid through the cannula to establish a fluid pool in front of the open end of the optical fiber, applying laser radiation through the optical fiber to the fluid pool and surrounding tissue, and slowly withdrawing the metallic cannula and the optical fiber from the region of application of the laser light during the application of the laser radiation. Preferably, the chosen physiologically acceptable fluid is continuously flowed through the open end of the metallic cannula during the application of the laser radiation through the optical fiber. Preferably also, the flow of fluid is substantially proportional to the laser intensity employed. It is preferred that the temperature of the treated tissue mass is monitored during the application of the laser radiation thereto.

Benefits and advantages of our invention include rapid necrosis of treated tissue, very high transmission efficiency of laser radiation being maintained during the procedure, and minimum damage to healthy tissue resulting from the insertion of the apparatus into a deeply-seated tumor mass.

BRIEF DESCRIPTION OF THE DRAWINGS

The accompanying drawing, which is incorporated in and forms a part of the specification, illustrates one embodiment of the present invention and, together with the description, serves to explain the principles of the invention. FIG. 1 shows a schematic representation of the side view of the apparatus of the present invention illustrating the metallic cannula, the optical fiber, and a commercially available "Y" connector for providing support for the cannula, longitudinal positioning for the fiber, and site for introduction of the physiologically acceptable fluid flow through the cannula. FIG. 2 is a detailed view of the distal end of the system, shown as the dashed enclosure in FIG. 1.

DETAILED DESCRIPTION OF A PREFERRED EMBODIMENT OF THE INVENTION

Briefly, the present invention includes an apparatus and method for performing interstitial therapy on malignant tissue masses whereby laser radiation is utilized to locally heat a tumor with resulting hyperthermia and necrotic coagulation. Laser energy transmission through an optical fiber is preserved by protecting the fiber using an ultra-thin metallic cannula through which a suitable fluid is para-axially flowed at room temperature, and by withdrawing the cannula/fiber combination slowly as the irradiation proceeds. Reference will now be made in detail to the present preferred embodiment of the invention, and example of which is illustrated in the accompanying drawing. FIG. 1 is a schematic representation of the side view of the preferred embodiment of our invention. A continuous-wave Nd:YAG laser 10 generates radiation which is coupled into a 600 micron diameter quartz optical fiber 12. The fiber has a divergence angle of 8°, and was stripped of its terminal 5 cm of plastic coating and the stripped 5 cm inserted into a 5 cm long, extra-thin 19 gauge needle 14 (less than 1 mm o.d., and less than 100 micron wall thickness) through a commercially available "Y" shaped connector 16. The internal diameter of the needle or cannula was sufficiently large to allow for easy location of the optical fiber as well as to permit coaxial flow of a cooling fluid such as normal saline. This fluid also provides a heat transfer medium for the laser energy exiting the optical fiber and the tissue under treatment, thereby avoiding direct heating of the tissue. Clearly, smaller diameter optical fibers can be employed for the purposes of the present invention, thereby allowing smaller cannulae to be used. This significantly diminishes the adverse effects of insertion of the apparatus into deeply-lying tumors on healthy tissue. Additionally, longer length cannulae may be employed in order to reach tissue masses to be treated which are distant from the skin surface. Prior to insertion, the position of the quartz fiber in the cannula without its stylet was adjusted such that the tip of the fiber 18 was approximately flush with the tip of the cannula 20 before tightening the proximal screw 22 of connector 16. It was found that if the fiber tip was located significantly inside of the cannula, excessive heating resulted, while if the tip was located significantly forward of the cannula tip, the cooling fluid was ineffective. The second arm 24 of connector 16 was attached to a fluid pump 26 which provided a selected fluid flow rate through the cannula. A thermocouple 28 was attached to a second, identical 5 cm needle 30, and was positioned approximately 3 mm lateral to and 3 mm forward of the optical fiber tip 18 in order to monitor and record 32 temperature changes in the vicinity of the optical fiber tip.

Having generally described the apparatus of the present invention, the following example will more particularly illustrate its features and method of its employment.

EXAMPLE

Malignant mammary gland tumors were induced in rats by injection of N-methyl-N-nitrosurea. Tumors measuring about 2 cm in diameter were chosen for in vivo treatment. Two 1 mm stab incisions were made 3 mm apart at suitable points near the longitudinal axis of the tumor to facilitate the insertion of the two needles 14, 30 which were fastened together approximately 5 cm from the end 20 of the cannula 14 containing optical fiber 12. The needles were then inserted into the tumor, traversing its length until thermocouple 28 could be palpated subcutaneously on the opposite pole of the tumor. Care was taken to place cannula 14 centrally and the thermocouple-carrying cannula 30 off center of the tumor axis. A stylet initially utilized to insert cannula 14 is then removed, and optical fiber 12 inserted to its predetermined position. A few drops of saline were allowed to flow in order to displace any air entrained in the cannula. Finally, the irradiation cannula/thermocouple assembly was attached to a lathe to regulate its withdrawal from the tumor while the laser energy was being applied to the tumor. At the onset of the experiment, approximately 0.2 ml of saline was allowed to flow in order to flush out tissue debris or blood clots in the needle cannula as well as to establish a fluid pool or bolus 34 in front of the optical fiber tip 18. This prevented contact between the optical fiber and the tumor tissue. This small bolus and the maintenance thereof by a constant flow rate proportional to the applied laser power output is essential for the preservation of the tip integrity and to subsequent successful transmission of the laser energy. The starting temperature was recorded and about 500 Joules of energy applied to the optical fiber at a rate of approximately 5 watts in 100 seconds while a saline flow of 1 ml per minute was maintained. It was determined that the laser energy exiting the optical fiber was approximately 93% of that applied thereto. Moreover, the transmission loss measured after a given procedure was completed was found to be about 2%. This compares well with transmission losses of 30–40% reported using other techniques. It should be mentioned that if a small bolus of fluid is admitted to the tissue in front of the fiber tip and no flow is allowed during the procedure, the transmission losses increase to about 7% with damage to the tip resulting. The withdrawal speed of the needle/fiber complex was adjusted so that the tip was pulled back about 10 mm during a typical irradiation period. Temperature was recorded continuously. At the end of an irradiation, the fiber transmission was measured using a power meter, and the tip integrity inspected under a microscope for loss of shine, dark spots or fracture. Forty-eight hours after the procedure, the tumor was excised and its volume determined by fluid displacement. Subsequent to the determination of the volume, the tumor was fixed in 10% formalin for later sectioning in order to determine the volume of necrosis/coagulation.

After many irradiation studies, it was concluded that the optimum rate of saline flow which minimizes the probe tip damage and prevents excessive edema of the tumor, while being effective at destroying tumor tissue was approximately 1 cc per minute at 5 Watts of laser power applied to the optical fiber. The comparable rates for 2.5, 7.5, and 10 Watts were found to be 0.5, 1.5, and 2 cc per minute, respectively. The laser probe transmission loss remained less than 3% for all of these laser power levels and 500 Joules of delivered energy. Damage to the optical fiber tip was observed whenever a. the saline flow was impeded, or b. the rate of fiber/cannula withdrawal was stopped or inadvertently slowed. In either situation, the accompanying thermocouple would warn of impending damage by indicating temperatures approaching 50° C. For experiments conducted with 5 Watts of laser power, the recorded tumor temperature 3 mm away from the fiber tip rose from an average base recording of 31° C. to a peak of 41° C. with a mean value of 8° C. for 10 experiments. Higher temperatures were observed for higher applied laser power levels despite an increase in saline flow rate, an increase in rate of withdrawal of the fiber/cannula assembly, and a decrease in irradiation time. At a power level of 2.5 Watts, the mean temperature rise was 1.5° C. Therefore, a direct relationship was observed to apply between the rise in the tumor temperature and the increase in laser power.

Exact measurement of the lesions was difficult both by eye and under the microscope since, in most experiments, islands of coagulation necrosis were found outside the main area of laser necrosis. The diameter of the lesions varied between 5 and 8 mm and the calculated volume of the entire lesion for 500 Joules of deposited energy was between 200 and 250 cubic mm. In the control group, the volume of necrotic tissue, either due to needle trauma or spontaneous necrosis, was estimated to be less than 10 cubic mm. According to the teachings of the present invention, a 2 cm diameter tumor can be coagulated in 5–10 min., while other techniques would take 30–40 min. Time is essential if multiple tumors are to be treated.

The withdrawal of the cannula during the application of laser energy to the tissue mass was found to have two advantages. First, the optical fiber was constantly being relocated into a cooler zone in the tumor, thereby reducing the cooling requirements of the coaxially-flowed fluid. Second, as successive regions of tumor were treated, coagulated column of necrotic tissue was generated, rather than a sphere of coagulation, which would have resulted if the optical fiber tip was kept stationary. Power levels of up to 10 Watts enabled significant volumes of tissue to be coagulated. For example, 1 cc was coagulated in less an two minutes. This has importance when one wishes to treat metastatic tumors measuring between 2 and 5 cm in diameter in solid organs such as the liver, where using the subject procedure, one may use a single needle by reinserting it at several points within the tumor under control by ultrasound. Real time sonographic and thermographic monitoring are essential for satisfactory ablation of all parts of the tumor. The present procedure may be performed either percutaneously or under direct visional laparotomy. An additional advantage of the present invention is the use of the same fine diagnostic needle (cannular and trocar) for introduction of the fiberoptic probe and laser energy into the target tumor. A 19 gauge ultra-thin needle 10–15 cm in length may be employed along with a 600 micron diameter quartz fiber to reach tumors located deeply within the body with minimal trauma. Previous investigators have used trocars or plastic sheaths with external diameters between 2 and 6 mm, rendering the target entry traumatic and the procedure hazardous.

The foregoing description of a preferred embodiment of the invention has been presented for purposes of illustration and description. It is not intended to be exhaustive or to limit the invention to the precise form disclosed, and obviously many modifications and variations are possible in light of the above teaching. For example, it would be apparent to one having skill in the art of laser heating, after having examined the present disclosure, that the use of a laser radiation absorbing biocompatible dye such as methylene blue, mixed with the saline solution would improve the laser coupling to the fluid bolus in front of the optical fiber tip and reduce the direct absorption of the radiation by the surrounding tissue, thereby enhancing the tissue coagulation effect of the Nd:YAG laser radiation. The embodiment was chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What we claim is:

1. An apparatus for interstitial laser therapy, which comprises in combination:

a. at most a single thin cannula for penetration and insertion into a tissue mass to be treated, and for delivering a chosen physiologically acceptable liquid to the tissue mass;

b. means for generating laser light having a chosen wavelength and intensity;

c. an optical fiber in communication with said light generating means for receiving and transmitting the laser light from said light generating means to the tissue mass, said optical fiber for placement within said single cannula such that the chosen liquid may be passed coaxially between said single cannula and said optical fiber;

d. means for adjustably securing the longitudinal location of said optical fiber within said single cannula; and e. a liquid pump in communication with the single cannula for flowing the chosen liquid through said single cannula and into the tissue mass.

2. The apparatus as described in claim 1, further comprising said physiologically acceptable liquid, wherein said physiologically acceptable liquid includes a dye which absorbs laser radiation having the chosen wavelength.

3. The apparatus as described in claim 2, wherein said physiologically acceptable liquid includes methylene blue.

4. A kit for interstitial laser therapy, which comprises:

a. at most a single first thin cannula for penetration and insertion into a tissue mass to be treated, and for delivering a chosen physiologically acceptable liquid to the tissue mass;

b. means for generating laser light having a chosen wavelength and intensity;

c. an optical fiber in communication with said light generating means for receiving and transmitting the laser light from said light generating means to the tissue mass, said optical fiber for placement within said single first cannula such that the chosen liquid may be passed coaxially between said single first cannula and said optical fiber;

d. means for adjustably securing the longitudinal location of said optical fiber within said single first cannula;

e. a liquid pump in communication with the single first cannula for flowing the chosen liquid through said single first cannula and into the tissue mass; and f. temperature measurement means for determining the heating effects of the laser light on the tissue mass, said temperature measurement means being attached to a second thin cannula which is inserted into the tissue mass and located in the vicinity of the end of said single first cannula.

* * * * *